US00PP17911P3

(12) United States Plant Patent

Clark et al.

(10) Patent No.: US PP17,911 P3

(45) Date of Patent: Aug. 7, 2007

(54) PEACH TREE—NAMED 'WHITE ROCK' CULTIVAR

(50) Latin Name: *Prunus persica*
Varietal Denomination: White Rock

(75) Inventors: John Reuben Clark, Fayetteville, AR (US); James Norman Moore, Fayetteville, AR (US)

(73) Assignee: University of Arkansas, division of Agriculture, Fayetteville, AR (US)

( * ) Notice: Subject to any disclaimer, the term of this patent is extended or adjusted under 35 U.S.C. 154(b) by 43 days.

(21) Appl. No.: 11/137,623

(22) Filed: May 25, 2005

(65) Prior Publication Data

US 2006/0272062 P1 Nov. 30, 2006

(51) Int. Cl.
*A01H 5/00* (2006.01)

(52) U.S. Cl. ..... Plt./195

(58) Field of Classification Search ..... Plt./194, Plt./195

See application file for complete search history.

*Primary Examiner*—Anne Marie Grunberg
*Assistant Examiner*—S. B. McCormick-Ewoldt

(57) ABSTRACT

Description and specifications of a new and distinct peach variety which originated from seed produced by a hand pollinated cross of Ark. 371 (non-patented) and Ark. 367 (non-patented) is provided. This new peach variety can be distinguished by its features of early mid-season ripening, high yields of high-quality, attractive, clingstone, very firm white-flesh fruits, and good plant vigor along with good resistance to bacterial spot disease.

3 Drawing Sheets

Botanical classification: Genus/species: *Prunus persica.* Cultivar: 'White Rock'.

SUMMARY OF THE INVENTION

The new and distinct variety of peach originated from a hand-pollinated cross of Ark. 371 (non-patented)×Ark. 367 (non-patented) made in 1993 at the University of Arkansas Fruit Substation, Clarksville. The female parent plant used in this hybridization (Ark. 371) is a very firm-fruited with a somewhat crisp flesh texture white peach selection with other characters including clingstone pit adherence, low-acid flavor, medium fruit size and ripens approximately July 20. The male parent (Ark. 367) is a first, non-melting flesh type white peach with a more rubbery texture as found in canning-cling type fruits, and is also a clingstone, large fruited, and ripens about July 1. Neither parent selection has been publicly released and nor are they available in commerce. The instant variety differs from one or both parents in that it ripens approximately June 25, has a low-acid flavor, medium fruit size and a very firm, semi-crisp flesh texture. Both the parents and the instant variety are the genus and species *Prunus persica.*

The seeds resulting from this controlled hybridization were germinated in a greenhouse in the late winter 1993/early spring of 1994 and planted in a field on the University of Arkansas Fruit Substation, Clarksville, Ark. The seedlings fruited during the summer of 1997 and one, designated Arkansas 658, was selected for its very firm white flesh, early mid-season ripening, large fruits, attractive fruit appearance, good fruit quality with low-acid flavor, and resistance to bacterial spot. During 1997, the original plant selection was propagated asexually, at the above-noted location, by budding onto standard peach rootstock variety 'Lovell' (non-patented) and a test plot of two plants was established. Subsequently, larger test plantings have been established with asexually multiplied plants at two additional locations in Arkansas (Clarksville and Hope, Ark.).

The new variety has been asexually multiplied several times since 1997 at this location by budding onto 'Lovell' peach rootstock and no incompatibility with peach rootstocks has occurred following budding. During all asexual multiplication, the characteristics of the original plant have been maintained and no aberrant phenotypes have appeared.

Plants of the new variety are vigorous and productive, and trees are standard in size, well-branched and symmetrical with an upright to semi-spreading growth habit, comparable to other peach trees (*Prunus persica*). Trees express a moderate level of resistance to both foliar and fruit infection of bacterial spot [*Xanthomonas campestris* pv. *pruni* (Smith) Dye] but in some years do not show complete immunity to this disease. The new variety consistently is more resistant to bacterial spot than is the standard white peach variety 'Carolina Belle' (not patented). The new variety blooms on approximately the same date as 'Carolina Belle' and 'Stark® Summer Pearl™' (not patented). No winter cold injury has been observed on wood or buds of the new variety in Arkansas tests where minimum temperatures have reached −13° C. during evaluation. Chilling requirement to break dormancy is estimated to be 750 hours below 7° C.

Fruit of the new variety ripens early mid-season, averaging 15 days before 'Carolina Belle' and 30 days before 'Stark® Summer Pearl™' reference white peach varieties. Average first ripening date is June 25 in west-central Arkansas (Clarksville). Fruit of the new variety has not been observed to have split pits, a serious fruit disorder of some peach varieties. Fruit yields have been good and have averaged higher than or near equal those of the comparison peach varieties 'Carolina Belle', and 'Stark® Summer Pearl™' in test comparisons.

The fruit is round to slightly oval in shape, without a prominent tip but with a pronounced suture bulge. Fruits are attractive with an average 72% bright red blush, and 28% white or cream skin background color. In some years the red blush was up to 80% of the fruit skin surface, especially when fruits are exposed to more sunlight than those fruits growing in the shaded canopy. Fruit finish is good with no blemishes. The fruit skin has average pubescence like other peaches. The flesh of the fruit is white in color and has slight red pigment in the flesh, mostly around the stone or pit. Flesh is non-melting to crisp in texture and is very firm and retains firmness after full maturity. The fruit is a clingstone, in that the flesh adheres to the pit. Fruit size is medium-large averaging 154 g.

The fresh fruit rates very good in flavor, and was rated highly in evaluations. Fruits average 12.2% soluble solids. The flavor is sweet and low-acid, with a light white peach aroma.

The distinctive features of the new variety are its early mid-season ripening, high yields of high-quality, attractive, clingstone, very firm white-flesh fruits, and good plant vigor along with good resistance to bacterial spot disease.

The new variety has been named the 'WHITE ROCK' cultivar.

BRIEF DESCRIPTION OF THE PHOTOGRAPHS

The accompanying photographs show typical specimens of the fruit (FIGS. 1 and 2) and leaf (FIG. 3) of the new variety in color as nearly true as it is reasonably possible to make in a color illustration of this character.

DETAILED BOTANICAL DESCRIPTION OF THE NEW VARIETY

The following is a detailed description of the botanical and pomological characteristics of the subject peach. Color data are presented in Royal Horticultural Society Colour Chart designations.

Where dimensions, sizes, colors and other characteristics are given, it is to be understood that such characteristics are approximations of averages set forth as accurately as practical.

The descriptions reported herein are from specimens grown at Clarksville, Ark. and are from trees grown in trickle (drip) irrigated orchards growing on a Linker fine sandy loam soil. The data were collected from six-year old trees of the instant variety except yield data that were taken on five-year-old trees in a replicated test planting.

Plant:

*Size.*—Mature trees (6 years of age and older) average 3.2 m to 3.5 m in height and 4.7 to 5.8 m in spread or width, and a semi-upright growth habit; as grown on 'Lovell' rootstock using an open-center training system commonly used on peaches. Tree size is comparable to that of the 'Carolina Belle' and 'Stark® Summer Pearl™' varieties.

*Growth.*—Vigorous, symmetrical form, good canopy development. Vigor comparable to that of the 'Carolina Belle' and 'Stark® Summer Pearl™' varieties.

*Productivity.*—Productive and consistent from year to year. Yield measured 25.5 kg/tree on five year-old trees trained to a perpendicular V training system, exceeding that of 'Carolina Belle' with 20.8 kg/tree and 11.0 kg/tree for 'Summer Pearl'™.

*Cold hardiness.*—Wood and dormant buds hardy to −13° C.; hardiness may exceed this level as this was the lowest temperature the trees were exposed to during testing.

*Disease resistance.*—Leaves and fruit resistant but not immune to bacterial spot under growing conditions where bacterial spot infection is often very severe on susceptible genotypes. No bactericides were used in the development or evaluation of the instant cultivar. Evidence of bacterial spot infection was less than that of 'Carolina Belle' in all years of evaluation. A commercial fungicide program was utilized in orchards used in the development and evaluation of the instant variety, thus no resistance to brown rot or peach scab, the other common diseases at Clarksville, Ark., was determined.

*Insect resistance.*—Insecticides were applied to orchards used in the development of the instant variety to control the common insects at the location including oriental fruit moth, plum curculio, stinkbug, tarnished plant bug, lesser peach tree borer, and greater peach tree borer. Therefore no insect resistance was determined in the testing of the instant variety.

Foliage/shoots/branches:

*Shoots.*—Smooth. Current growing-season mature shoot length 42.6 cm; diameter base 0.52 cm, midpoint 0.38 cm, terminal 0.28 cm (measured in July of the growing season). Dormant-season shoot (branch): length 42.6 cm; diameter at base 0.56 cm; diameter at midpoint 0.41 cm; diameter at terminal 0.29 cm. Dormant-season shoot color Greyed-Purple Group (183B); Dormant-season shoot texture smooth.

*Leaves.*—Simple, alternate, glabrous, lanceolate, petiolate, deciduous. Venation pinnate; base acute; terminal or apex acuminate; margin serrated. Mature leaf size: length 15.8 cm; width midpoint 4.0 cm. Leaf serrations; 4.4/cm. Mature leaf color: abaxial — Yellow-Green Group (146B); adaxial — Yellow-Green Group (137B); and anthocyanin not present on abaxial or adaxial side of mature leaves on midrib or other location. Young leaf color: abaxial — Yellow-Green Group (146B); adaxial — Yellow Green Group (146A); anthocyanin not present on abaxial or adaxial side of young leaves on midrib or other location. Petiole length — mature leaf: 1.1 cm. Leaf glands: reniform, 2 per leaf usually, located on basal portion of leaf blade. Leaf glands are 0.06 cm in width and 0.12 cm in length.

*Buds.*—Number of leaf buds per 15 cm: 8.4 evenly distributed along the shoot. Number of flower buds per 0–15 cm from terminal: 12.6. Mature shoot internode length between buds: base 1.4 cm, midpoint 1.8 cm, terminal 1.1 cm.

Bark (of mature trunk of tree):

*Color.*—Greyed-Green Group (197B).

*Texture.*—Rough.

Trunk:

*Diameter.*—14 cm (at 25 cm above ground level).

Flower buds: Dormant flower bud length 0.4 cm and diameter 0.2 cm and color Greyed-Orange Group (166A); dormant buds swell and expand in late winter and increase in size during this expansion to fully open flowers. Color changes to that of the adaxial petal color Red-Purple Group (65C).

Flowers: Bloom occurs prior to vegetative bud break; solitary to occasional double individual flowers at a single node; perfect; self-fertile.

*Date of bloom.*—First, Julian 80 (March 20); Full, Julian 87 (March 27).

*Size.*—Diameter fully open 3.9 cm.

*Type.*—Showy.

*Color.*—Adaxial — Red-Purple Group (65C); abaxial — Red-Purple Group (65D).

*Petals per flower.*—5.

*Length of pistil.*—1.7 mm.

*Stamens.*—Average 48/flower with pollen present, fertile and abundant.

Fruit:

*Size.*—Med-large, avg. 154 g; diameter stem end 4.8 cm, equator 6 cm, blossom end 4.0 cm; length base to apex 5.7 cm.

*Shape.*—Round to oval. Fruits are without pronounced tip but have a pronounced suture bulge.

*Skin.*—Pubescent (fuzzy), attractive; ground color Yellow Group (11B), with red blush (Red Group 46A; 47 D), over 72% of surface on average.

*Flesh.*—Yellow-White Group (158C); cling; non-melting texture; exceptional firmness. Firmness when measured by a fruit pressure tester (using a McCormick model FT327 fruit pressure tester, 11 mm diameter probe, McCormick Fruit Tree Co., Yakima, Wash.) on unpeeled fruit had average firmness value of 6.2 kg. Good eating quality; flavor sweet, low-acid, with light white peach flavor and aroma.

*Pedicel length.*—0.7 cm.

*Pedicel diameter.*—0.4 cm.

*Pedicel color.*—Yellow-Green Group (144C).

*Ripe date.*—First ripe June 25 (Julian 177) in west-central Arkansas. Ripening of individual fruit is uniform.

*Tendency of pit to split.*—No split pits observed.

*Soluble solids.*—12.2%.

*Fruit juice pH.*—4.82.

Pit/stone:

*Size.*—Length 3.4 cm; diameter (midpoint) 2.1 cm.

*Shape.*—Slightly oblong with deep furrowing and pitting.

*Color.*—Greyed-Orange Group (167C).

Kernel:

*Size.*—Length 1.5 cm; diameter varies with dryness of the kernel but is up to 0.4 cm.

*Shape.*—Almond shaped.

*Color.*—Greyed-Orange Group (163A).

Uses: Fresh consumption, not evaluated for drying or other uses.

The Variety

The most distinctive features of the new variety are its early mid-season ripening, high yields of high-quality, attractive, clingstone, very firm white-flesh fruits, and good plant vigor along with good resistance to bacterial spot disease.

We claim:

1. A new and distinct variety of peach tree (*Prunus persica* cultivar 'White Rock') as herein described and illustrated, characterized by its early mid-season ripening, high yields of high-quality, attractive, clingstone, very firm white-flesh fruits, and good plant vigor along with good resistance to bacterial spot disease.

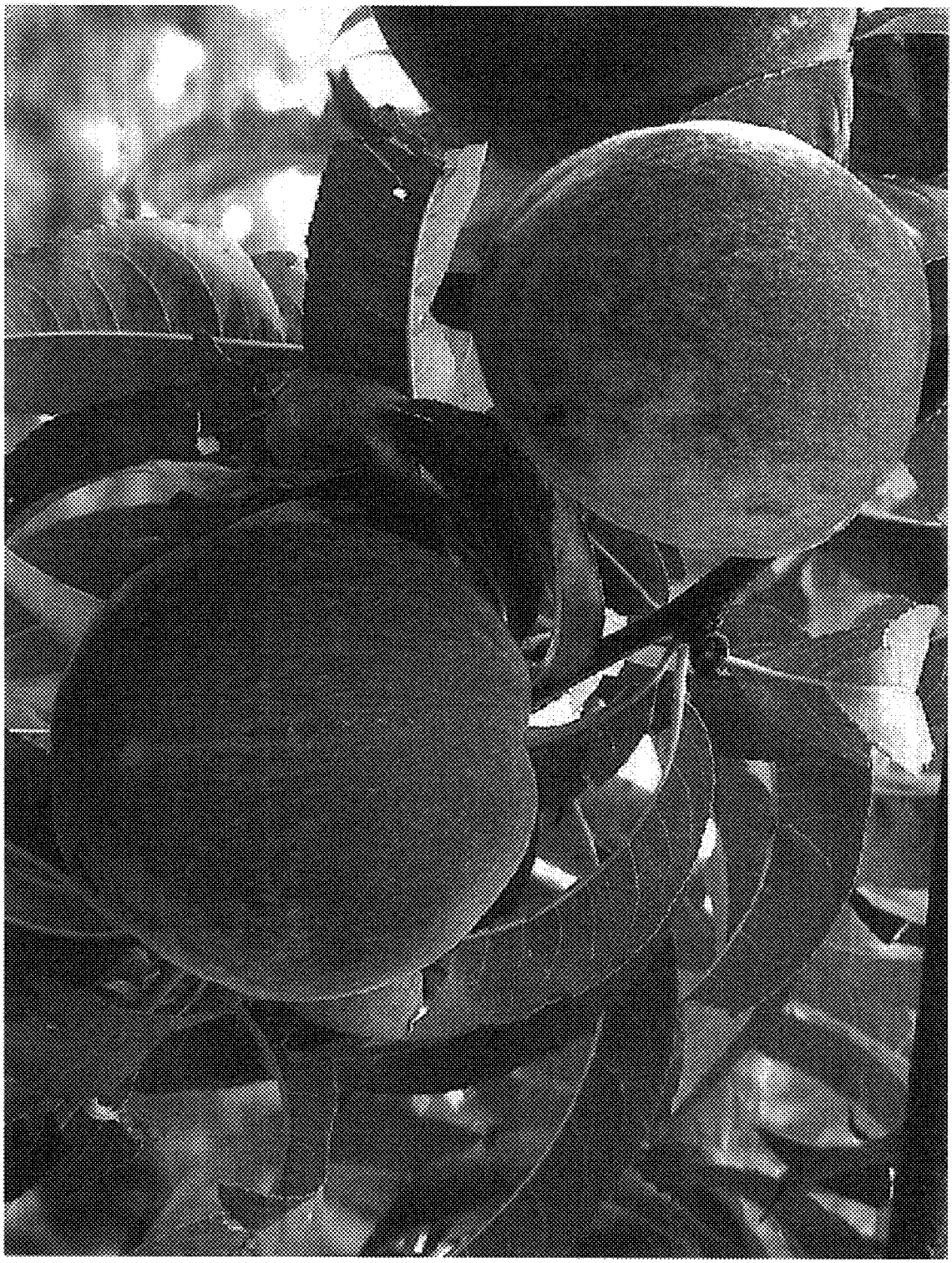

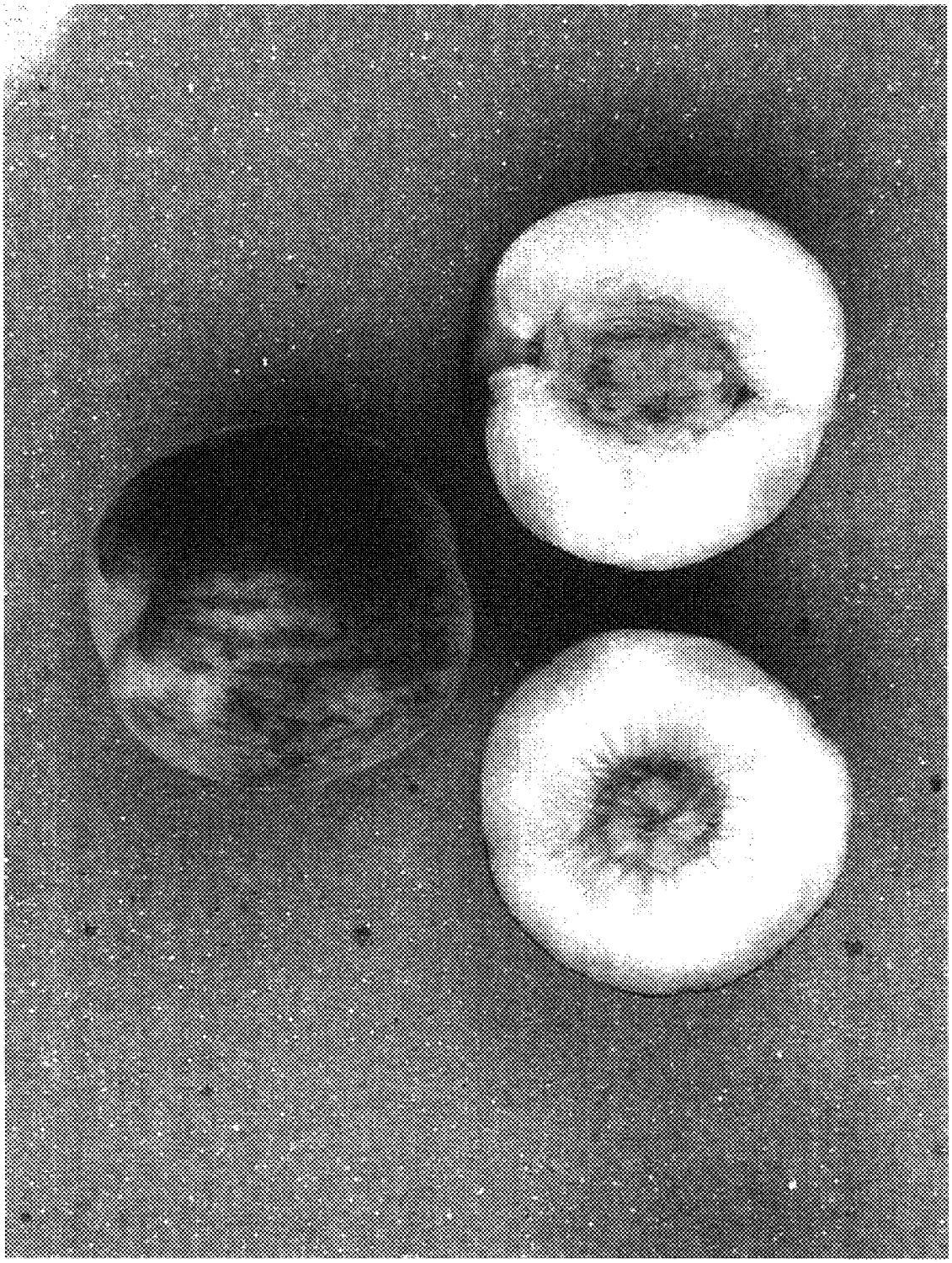

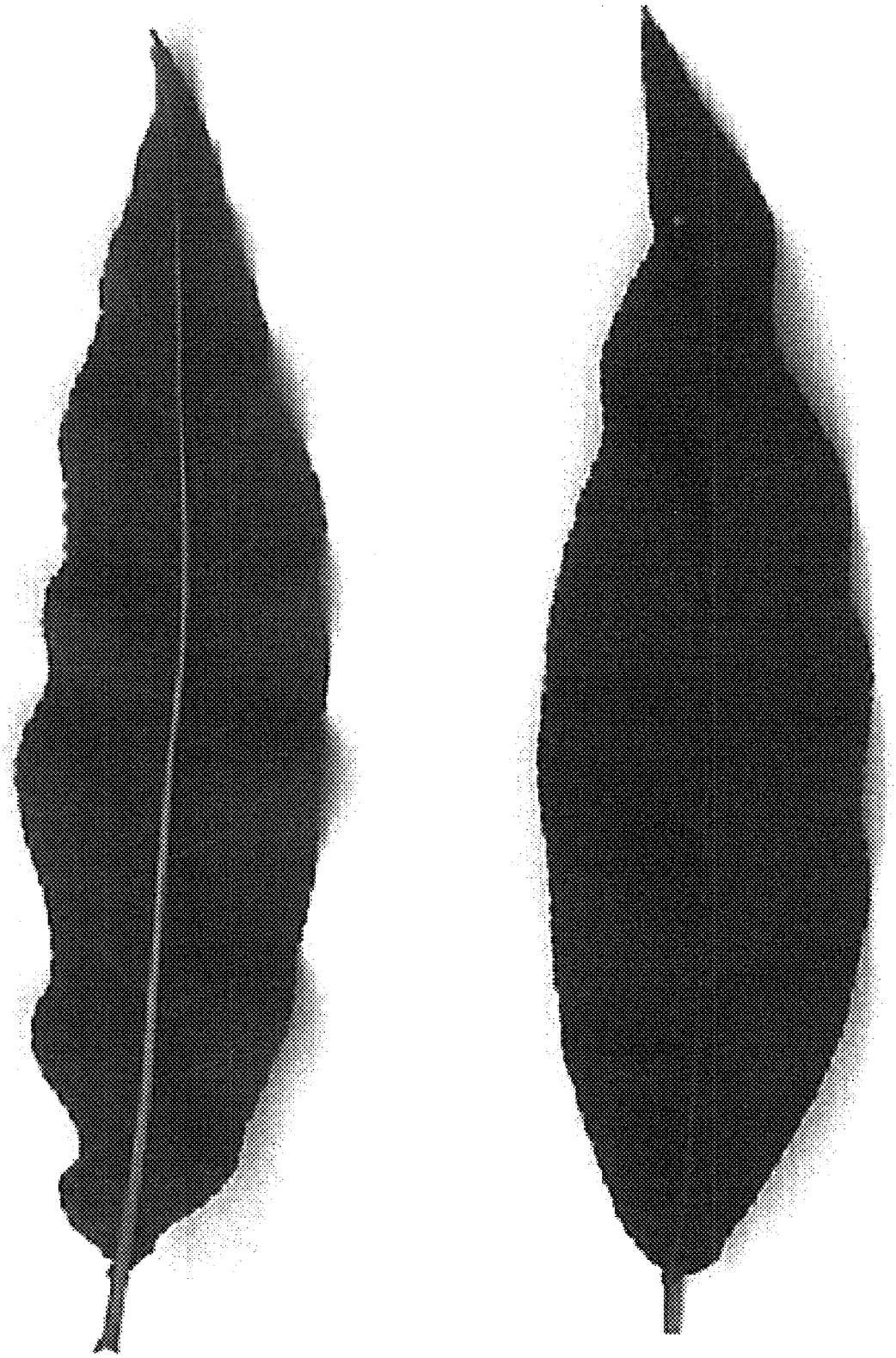

* * * * *